United States Patent
Aramata et al.

(10) Patent No.: US 6,365,766 B1
(45) Date of Patent: Apr. 2, 2002

(54) METALLIC COPPER CATALYST AND PROCESS FOR THE SYNTHESIS OF ORGANOHALOSILANES

(75) Inventors: Mikio Aramata; Masaaki Furuya; Yoshihiro Shirota; Akio Muraida; Susumu Ueno; Toshio Shinohara, all of Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/548,427

(22) Filed: Apr. 12, 2000

(30) Foreign Application Priority Data

Apr. 13, 1999 (JP) ............................................. 11-104693

(51) Int. Cl.$^7$ ................................................. C07F 7/16
(52) U.S. Cl. ...................... 556/472; 502/343; 502/345; 423/604
(58) Field of Search .......................... 556/472; 502/343, 502/345; 423/604

(56) References Cited

U.S. PATENT DOCUMENTS 4,450,282 A * 5/1984 Ritzer et al. ................ 556/472
5,817,855 A * 10/1998 Langner et al. ............. 556/472
6,057,469 A * 5/2000 Margaria et al. ............ 556/472
6,218,562 B1 * 4/2001 Aramata et al. ............ 556/472
6,239,304 B1 * 5/2001 Aramata et al. ............ 556/472

FOREIGN PATENT DOCUMENTS

| JP | 9-173844 | 7/1997 |
| JP | 10-309465 | 11/1998 |

OTHER PUBLICATIONS

English Abstract of JP 10–309465, Nov. 1998.

English Abstract of JP 9–173844, Jul. 1997.

* cited by examiner

*Primary Examiner*—Paul F. Shaver
(74) *Attorney, Agent, or Firm*—Millen, White, Zelano & Branigan, P.C.

(57) ABSTRACT

Organohalosilanes are prepared by reacting an organic halide with metallic silicon particles in the presence of a metallic copper catalyst which is a metallic copper powder in flake form having a bulk specific gravity of 1–3 g/cm$^3$ and a mean particle size of 10 $\mu$m to 1 mm as measured by laser diffraction particle size distribution analysis.

3 Claims, 2 Drawing Sheets

METALLIC COPPER CATALYST AND PROCESS FOR THE SYNTHESIS OF ORGANOHALOSILANES

This invention relates to a process for preparing organohalosilanes according to the Rochow reaction and a copper catalyst used therein.

BACKGROUND OF THE INVENTION

In the industry, the Rochow reaction is typically employed for the synthesis of organohalosilanes such as methylchlorosilanes. That is, direct reaction of organic halides such as alkyl halides and phenyl halides with metallic silicon particles is carried out at 250 to 500° C. in the presence of a copper catalyst. The key technology in this reaction for the synthesis of methylchlorosilanes is to increase the selectivity of the most demanded dimethyldichlorosilane. And for the synthesis of phenylsilanes, the key is to yield desirable diphenyldichlorosilane and phenyltrichlorosilane in a composition complying with the demand.

More particularly, organohalosilanes are synthesized by the Rochow reaction of passing an organic halide gas such as methyl chloride through a contact mass comprising metallic silicon, copper catalyst and a minor amount of co-catalyst to effect direct reaction in a gas phase. In this reaction, it is important to increase the reaction rate of metallic silicon because the cost of metallic silicon is predominant among the raw material cost. Since a variety of by-products usually form in addition to the desired diorganodichlorosilane, it is also important to control reaction conditions so that the proportion of these by-products may comply with the supply/demand balance of organochlorosilanes. Industrially, this reaction is generally carried out in a reactor such as a fluidized bed, vibrating fluidized bed or agitating fluidized bed while replenishing the contact mass to the reaction system. Requisite considerations on this reaction are to reduce the time taken for activation until the reaction reaches a steady state (that is, activation time), to prevent lowering of catalytic activity due to deposition of deactivated contact mass with the progress of reaction (that is, lowering of reaction rate and selectivity), and to minimize the amount of reactor residues (high-boiling fractions such as disilanes) which are unnecessary.

However, the conventional Rochow reaction requires a very long time for activation until the reaction reaches a steady state. The steady state, in turn, is relatively short. The yield of dimethyldichlorosilane decreases with the lapse of time because of carbon deposition on the contact mass surface due to side-reaction. In the synthesis of methylsilanes, for example, high-boiling fractions such as disilanes and undesired products such as methyltrichlorosilane increase due to side-reaction, resulting in low reaction yields.

JP-A 10-309465 discloses that it is effective to add a copper catalyst to this reaction system after metallic silicon power alone is previously heated near the reaction temperature. As understood from this disclosure, only the active copper catalyst is necessary. The deactivated catalyst merely contributes to the formation of carbon and side reaction to increase the amount of $Me(H)SiCl_2$ and the ratio of $MeSiCl_3/Me_2SiCl_2$. It is then important to reduce the residence time of the copper catalyst and remove the copper catalyst once deactivated.

However, merely reducing the particle size of the copper catalyst is ineffective for reaction in a fluidized bed or agitating fluidized bed because the catalyst is carried with the stream of unreacted reactant gas and produced silane vapor away from the reaction system without acting as the catalyst. It is thus desired to have a catalyst which resides within the system while it is active, but once deactivated, is immediately discharged out of the system.

In the reaction of this sort, the copper catalyst is mixed with metallic silicon powder and acts on an alkyl halide (e.g., methyl chloride) or aryl halide (e.g., benzene chloride) to produce a corresponding organohalosilane. This reaction is basically a gas-solid heterogeneous reaction between the organic halide which is gaseous and the copper catalyst and metallic silicon powder which are solid even at elevated temperature. It is then reasonably anticipated that the surface activity of the copper catalyst is important. With respect to the use of copper oxide as the catalyst in this reaction, powder parameters of the catalyst including surface area and particle size are referred to in U.S. Pat. Nos. 4,520,130, 4,504,597 and JP-A 9-173844. However, the morphology of the copper catalyst has not been discussed from the above-mentioned standpoint, much less the morphology of metallic copper catalyst.

SUMMARY OF THE INVENTION

An object of the invention is to provide a novel and improved metallic copper catalyst for use in the synthesis of organohalosilanes, which can be effectively discharged out of the reaction system once deactivated. Another object is to provide a process for preparing organohalosilanes using this catalyst.

With respect to the copper catalyst for use in the Rochow reaction, a study was made on the morphology of the copper catalyst which can be readily discharged out of the reaction system when it is deactivated so that it becomes useless for the Rochow reaction and rather causes side reaction. It has been found that when a copper powder in flake (metal foil) or scale form having a large surface area and a low bulk specific gravity which is available as ground or chopped powder of rolled metallic copper foil, or stamped copper powder obtained by stretching and milling rolled copper foil or machined copper plates as by stamping is used as the copper catalyst, this catalyst can be quickly discharged out of the reaction system once deactivated.

In a first aspect, the invention provides a metallic copper catalyst for use in the synthesis of organohalosilanes, consisting of a metallic copper powder in flake or scale form having a bulk specific gravity of 1 to 3 $g/cm^3$ and a mean particle size of 10 $\mu m$ to 1 mm as measured by laser diffraction particle size distribution analysis. Preferably, the metallic copper powder is a copper foil powder or stamped copper powder having a specific surface area of 0.1 to 2 $m^2/g$ as measured by the BET method or air permeability method.

In a second aspect, the invention provides a process for preparing organohalosilanes, comprising the step of reacting an organic halide with metallic silicon particles in the presence of the metallic copper catalyst defined above.

In connection with the Rochow reaction, that is, the organohalosilane synthesis reaction between an alkyl halide (e.g., methyl chloride) or aryl halide (e.g., benzene chloride) and metallic silicon in the presence of a copper catalyst and a co-catalyst (e.g., zinc or tin), the present invention uses the above-defined catalyst to solve the problem of the prior art technology that the activation time (or induction period) taken until the reaction rate and selectivity of silane synthesis reach a steady state is very long while the steady state continues relatively short. By studying the catalytic action and physical properties of the copper catalyst, the invention has succeeded in optimizing the morphology of a metallic copper catalyst. The invention overcomes the above-mentioned problems of the Rochow reaction and in particular, increases the selectivity of desired dimethyldihalosilane, and prolongs the steady state or increases the conversion rate of silicon, achieving improved reaction yields.

More particularly, the feature of the invention resides in the removal of the deactivated contact mass, especially deactivated copper catalyst from the reaction system. For the reaction to which the invention pertains, the copper catalyst is an essential component which is mixed with metallic silicon powder and helps the silicon react with an alkyl halide (e.g., methyl chloride) or aryl halide (e.g., benzene chloride) to form corresponding organohalosilanes. Since this reaction is basically a gas-solid heterogeneous reaction between the organic halide which is gaseous at elevated temperature and the copper catalyst and metallic silicon powder which remain solid even at elevated temperature, the copper catalyst must present a fresh active surface. However, the copper catalyst surface is deactivated with the progress of reaction. If the copper catalyst is merely deactivated from the reaction, it will give rise to no problem even when it continues to reside within the reaction system. On analysis of reaction states including produced silane composition and carbon deposition on the contact mass, however, it was found that in fact, the deactivated catalyst maintains activity to side reaction. It is, therefore, crucial to remove the copper catalyst from the reaction system immediately after deactivation.

The problem can be solved using copper powder (catalyst) in microparticulate form. However, simply using microparticulate copper powder is uneconomical because the majority of the copper powder is carried along with the stream of reactant gases and reaction products away from the reaction system before it exerts catalysis, which necessitates to feed a great excess of the copper catalyst. On the other hand, if copper particles having a large particle size are used, they will deposit and accumulate in the reaction system, giving rise to the above-mentioned problem. The particle size of copper powder that can clear both the problems is limited to a narrow range. In the Rochow reaction in which the particle size of metallic silicon reactant changes with the progress of reaction, it is in fact difficult to control the particle size of copper powder. This difficulty is eliminated by using as the copper catalyst a metallic copper powder in flake or scale form having a bulk specific gravity of 1 to 3 g/cm$^3$ and a mean particle size of 10 μm to 1 mm as measured by laser diffraction particle size distribution analysis, and more preferably, copper foil powder obtained by milling electrolytic copper foil or rolled copper foil, or stamped copper powder obtained by stretching and milling electrolytic copper foil, rolled copper foil or machined copper powder as by stamping, in flattened scale or flake form having a large specific surface area of 0.1 to 2 m$^2$/g as measured by the BET method or air permeability method. That is, the copper catalyst in a very thin scale or flake form is preferable as the catalyst for the direct silane producing method or Rochow reaction. This copper catalyst has a large air-permeability method specific surface area and/or BET method specific surface area, and once deactivated by reaction in the fluidized bed or agitating fluidized bed, it converts into fine particulate form so that it may be carried along with the stream of produced halosilanes and unreacted reactant gases and vapors away from the reaction system.

BRIEF DESCRIPTION OF THE DRAWINGS

FIG. 1 is photomicrographs of copper flakes according to the invention,

DESCRIPTION OF THE PREFERRED EMBODIMENTS

The copper catalyst of the invention is a metallic copper powder in flake or scale form having a bulk specific gravity of 1 to 3 g/cm$^3$ and a mean particle size of 10 μm to 1 mm as measured by laser diffraction particle size distribution analysis.

Figure 1A:
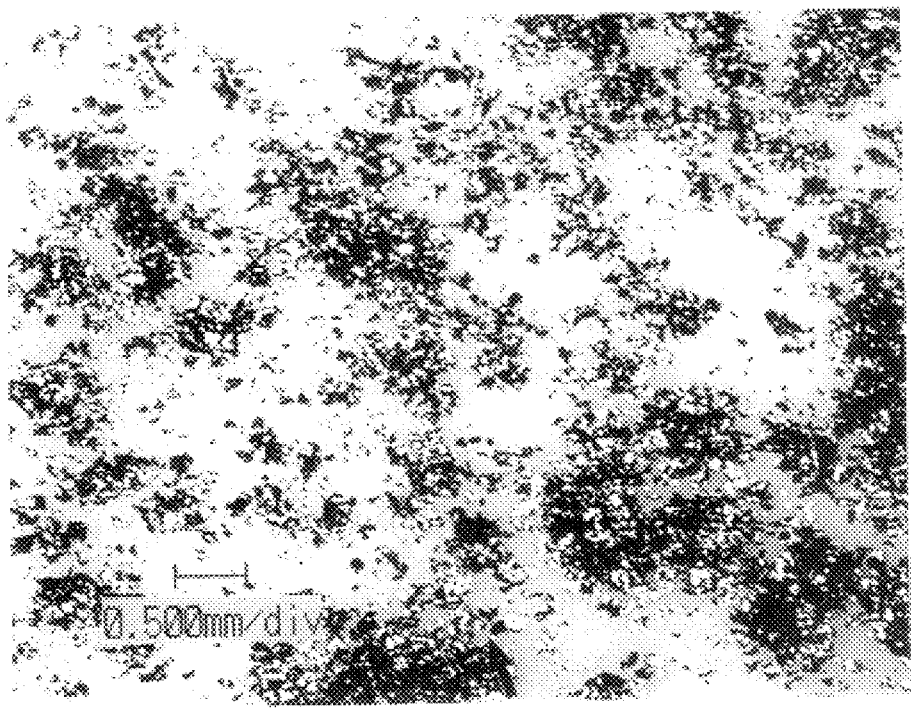
FIG. 1A being a photograph of magnification ×20 under an optical microscope.
Figure 1B:
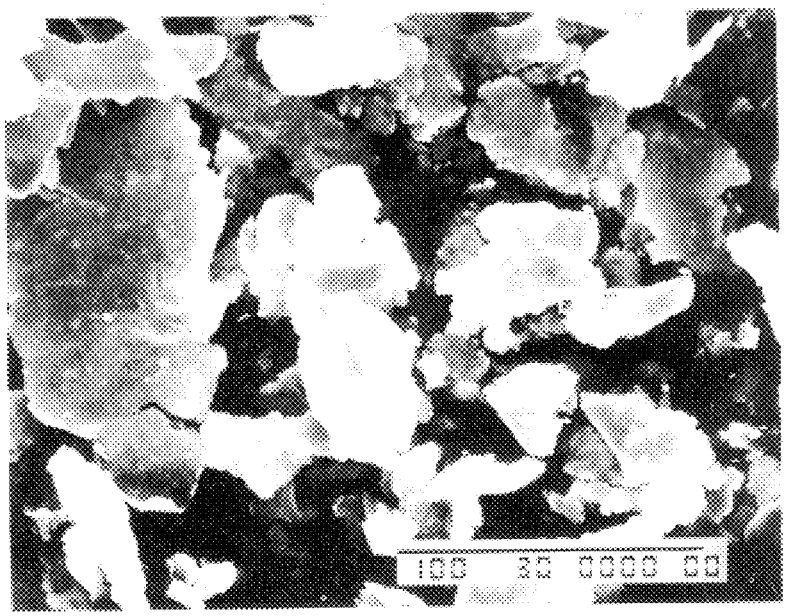
FIG. 1B being a SEM photograph of magnification ×400.

The copper catalyst is available as rolled copper powder obtained by milling rolled copper foil or as flake copper powder obtained by stamping rolled copper foil, electrolytic copper powder or machined copper chips because metallic copper is richly ductile. One exemplary form of metallic copper is shown in FIG. 1. FIG. 1A is a photograph (magnification ×20) of flake copper powder under an optical microscope and FIG. 1B is a SEM photograph (magnification ×400) of the same.

The copper flakes of the above nature are soft, but when heated to the reaction temperature of 250 to 500° C., are annealed so that they increase the hardness and become brittle. Through rigorous collision between contact mass particles by admixing and agitation in the fluidized bed or agitating fluidized bed during reaction, the copper flakes as annealed are rounded or fractured into copper fines. Given the steady state, by continuously supplying a fresh copper catalyst to the reactor along with a fresh metallic silicon powder, the deactivated copper catalyst (copper fines) can be continuously discharged out of the reaction system so that the active copper catalyst-containing contact mass composition is maintained. In fact, in an experiment using a small reactor of the laboratory size, flake copper powder was observed only at a short initial stage of reaction, but little observed within the reactor with the progress of reaction. Copper fines of reduced size are carried along with the stream of reactant gases and product silane vapors away from the reactor. In an experiment using a reactor sized for the industrial manufacture, the contact mass discharged out of the reactor had an extremely higher copper concentration than the copper concentration initially added to the system. On microscopic observation, the discharged contact mass contained no flakes, but fines.

The copper catalyst of the invention should have a bulk specific gravity of 1 to 3 g/cm$^3$ and preferably 1.5 to 2.5 g/cm$^3$. It is noted that conventional copper catalysts which are not in flake form have a bulk specific gravity of about 5.0 g/cm$^3$. Too high a bulk specific gravity indicates that copper powder is not in flake form suitable as the copper catalyst, failing to achieve the objects of the invention.

When particle size distribution is measured by laser diffractometry, the copper powder should have a mean particle size of 10 μm to 1 mm and preferably 20 to 100 μm.

Further preferably, the copper catalyst of the invention should have a specific surface area of 0.1 to 2 m$^2$/g and especially 0.2 to 1.0 m$^2$/g as measured by the BET method or air permeability method. Copper particles with too small a specific surface area are rather restrained from being finely fractured after deactivation whereas too large a specific surface area indicates easy scattering away from the fluidized bed to the outside.

Excepting the use of the above-defined copper catalyst, the organohalosilane preparing process of the invention may be carried out by employing any well-known procedure and conditions. For example, the metallic silicon particles used as one reactant may have a mean particle size of about 10 μm to about 10 mm. The organic halide used as the other reactant may be selected from alkyl halides and aryl halides having an alkyl or aryl group corresponding to a desired organohalosilane, for example, methyl chloride, ethyl chloride, and phenyl chloride. According to the invention, organohalosilanes of the following formula:

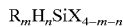

$$R_mH_nSiX_{4-m-n}$$

wherein R is $C_{1-4}$ alkyl or aryl such as phenyl, X is a halogen atom such as chlorine or bromine, and "m" is an integer of 1, 2 or 3, "n" is an integer of 0, 1 or 2, and m+n is an integer of up to 4, especially diorganodihalosilanes wherein m=2 and n=0, can be produced in high yields.

The amount of the copper catalyst added may be about 0.1 to about 10 parts by weight per 100 parts by weight of the metallic silicon. Any of well-known co-catalysts may be added to the copper catalyst.

Figure 2:
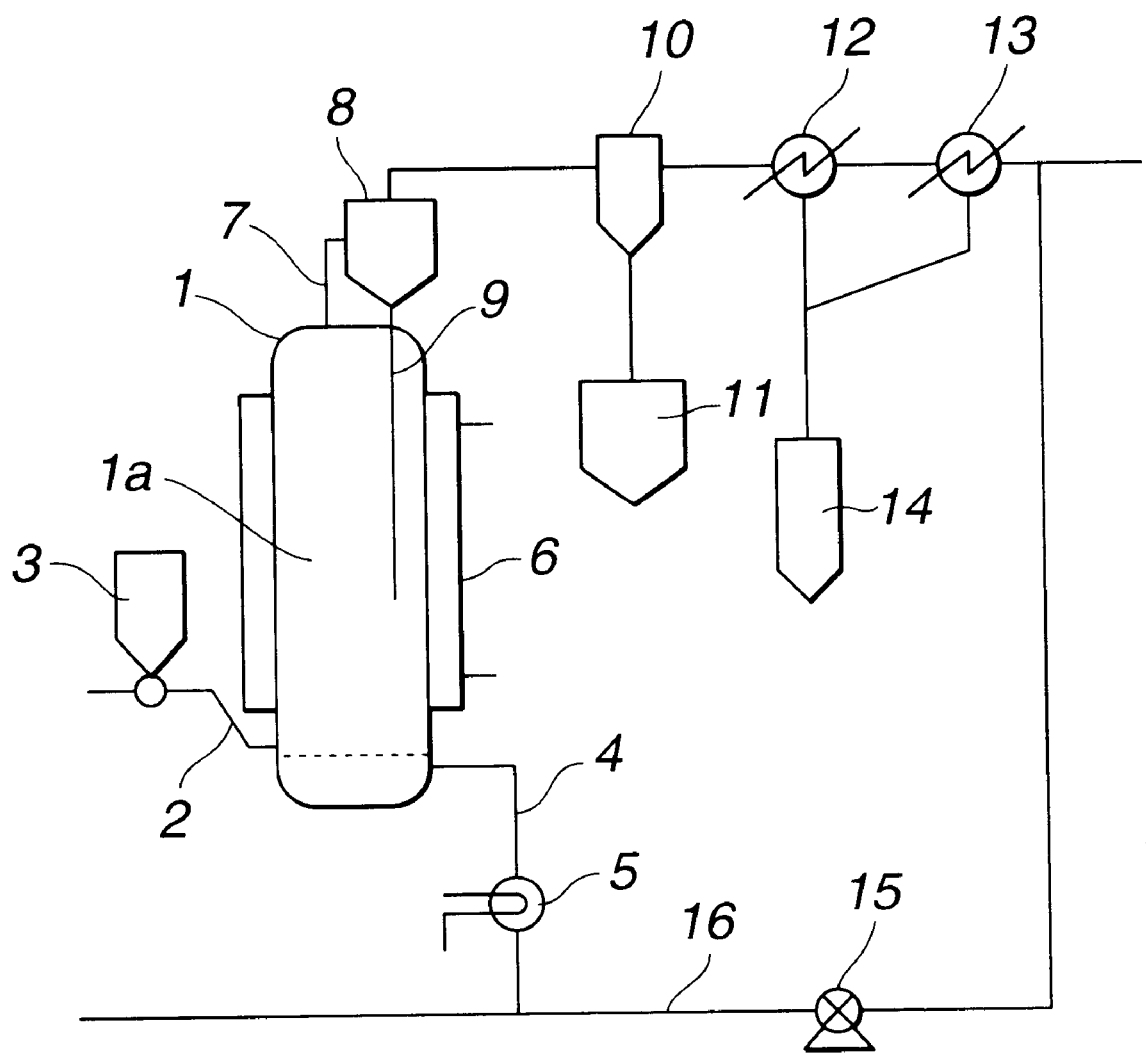
FIG. 2 schematically illustrates a system for the preparation of organohalosilanes.

FIG. 2 illustrates a system for preparing organohalosilanes. The system includes a fluidized bed reactor 1 and a reactant source tank 3 connected to the bottom of the reactor 1 through a reactant feed conduit 2, whereby metallic silicon and a copper catalyst or a mixture of a copper catalyst and a co-catalyst are admitted into the bottom of the reactor 1. A conduit 4 for the other reactant, organic halide has a heater 5 inserted therein and is connected to the reactor 1 at the bottom. The organic halide in gas or vapor form is also introduced into the bottom of the reactor 1, thereby forming a fluidized bed 1a of the metallic silicon and the catalyst within the reactor 1. The reactor 1 is enclosed with a cooling jacket 6.

Preferably the organic halide in gas or vapor form is introduced into the reactor 1 at a linear velocity of 2 to 10 cm/sec in the steady state. Reaction is generally carried out at a temperature of 250 to 350° C.

The organohalosilane product resulting from the reaction is channeled through a discharge conduit 7 connected to the top of the reactor 1 to a first cyclone 8 where the entrained solid particles are separated and fed back to the fluidized bed 1a through a return pipe 9. The product is then fed to a second cyclone 10 where the entrained solid particles are separated and fed to a particle reservoir 11 for storage. The product is then fed to first and second silane condensers 12 and 13 where the organohalosilanes are condensed and fed to a silane reservoir 14 for storage. Part or all of the discharge gas from which solid particles have been separated and organohalosilanes have been condensed and separated is fed back to the reactor 1 through an organic halide return conduit 16 having a recycle gas compressor 15 inserted therein. The return conduit 16 is connected to the organic halide feed conduit 4.

EXAMPLE

Examples of the invention are given below by way of illustration and not by way of limitation. All parts are by weight.

Example 1

Using a system as shown in FIG. 2, methylchlorosilanes were prepared. A steel reactor of 8 cm in diameter equipped with a spiral agitator was charged with 100 parts of metallic silicon powder having a mean particle size of 50 μm. With stirring by the spiral agitator, nitrogen gas was introduced into the reactor at a linear velocity of 2 cm/sec to fluidize the silicon powder while the powder was heated to 280° C. Thereafter, 3 parts of a catalyst mixture was added to the reactor. The catalyst mixture consisted of a copper catalyst in the form of a flake copper foil powder obtained by stamping, having an air-permeability method specific surface area of 0.80 m²/g, a mean particle size of 47 μm, and a bulk specific gravity of 1.9 g/cm³ and a co-catalyst composed mainly of brass and bronze. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. During reaction, the metallic silicon powder and the copper catalyst were continuously replenished in amounts corresponding to a consumption due to silane formation and a loss discharged out of the reactor. After 72 hours, the reaction was stopped. The average rate of silane production, percent consumption of metallic silicon, and the composition of the formed silanes are shown in Table 1.

Example 2

As in Example 1, the reactor charged with 100 parts of metallic silicon powder having a mean particle size of 50 μm was heated to 280° C. in a nitrogen gas stream. Thereafter, 3 parts of a catalyst mixture was added to the reactor. The catalyst mixture consisted of a copper catalyst in the form of a flake copper foil powder obtained by stamping, having an air-permeability method specific surface area of 0.80 m²/g, a mean particle size of 47 μm, and a bulk specific gravity of 1.9 g/cm³ and a co-catalyst composed mainly of an antimony alloy, brass and bronze. While the reaction temperature was controlled in the range of 280 to 300° C., methyl chloride was slowly added for reaction. After 72 hours, the reaction was stopped. The average rate of silane production, percent consumption of metallic silicon, and the composition of the formed silanes are shown in Table 1.

Example 3

As in Example 1, the reactor charged with 100 parts of metallic silicon powder having a mean particle size of 50 μm was heated to 280° C. in a nitrogen gas stream. Thereafter, 3 parts of a catalyst mixture was added to the reactor. The catalyst mixture consisted of a copper catalyst having an air-permeability method specific surface area of 0.55 m²/g, which had been prepared by annealing at 300° C. in nitrogen gas a copper catalyst in the form of flake copper foil powder obtained by stamping and having an air-permeability method specific surface area of 0.88 m²/g, and a co-catalyst composed mainly of brass and bronze. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. During reaction, the metallic silicon powder and the copper catalyst were continuously replenished in amounts corresponding to a consumption due to silane formation and a loss discharged out of the reactor. After 72 hours, the reaction was stopped. The average rate of silane production, percent consumption of metallic silicon, and the composition of the formed silanes are shown in Table 1.

Comparative Examples 1 and 2

As in Example 1, the reactor charged with 100 parts of metallic silicon powder having a mean particle size of 50 μm was heated to 280° C. in a nitrogen gas stream. Thereafter, 3 parts of a catalyst mixture consisting of a copper catalyst and a co-catalyst composed mainly of brass, bronze and antimony was added to the reactor. The copper catalyst used in Comparative Example 1 was a copper powder obtained by machining and stamping to induce some stretching and having an air-permeability method specific surface area of 0.10 m$^2$/g, a mean particle size of 105 μm and a bulk specific gravity of 3.5 g/cm$^3$. The copper catalyst used in Comparative Example 2 was an electrolytic copper powder having an air-permeability method specific surface area of 0.10 m$^2$/g, a mean particle size of 57 μm and a bulk specific gravity of 5.4 g/cm$^3$. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. During reaction, the metallic silicon powder and the copper catalyst were continuously replenished in amounts corresponding to a consumption due to silane formation and a loss discharged out of the reactor. After 72 hours, the reaction was stopped. In these examples, a small amount of the copper catalyst added was satisfactory. The average rate of silane production, percent consumption of metallic silicon, and the composition of the formed silanes are shown in Table 1.

TABLE 1

| | EX1 | EX2 | EX3 | CE1 | CE2 |
|---|---|---|---|---|---|
| Metallic copper form | flake foil powder | flake foil powder | flake foil powder, annealed | machined and somewhat stretched powder | electrolytic copper powder |
| Co-catalyst | Zn-Sn | Sb-Zn-Sn | Zn-Sn | Sb-Zn-Sn | Sb-Zn-Sn |
| Air-permeability method specific surface area (m$^2$/g) | 0.80 | 0.80 | 0.55 | 0.10 | 0.10 |
| Bulk specific gravity (g/cm$^3$) | 1.9 | 1.9 | 2.8 | 3.5 | 5.4 |
| Mean particle size (μm) | 47 | 47 | 35 | 105 | 57 |
| Average rate of silane production (g-silane/100 g-hr) | 16.8 | 17.5 | 9.5 | 5.3 | 2.5 |
| Me(H)SiCl$_2$ (%) | 2.2 | 2.0 | 6.5 | 9.5 | 10.3 |
| Me$_2$SiCl$_2$ (%) | 88 | 90 | 75 | 55 | 46 |
| MeSiCl$_3$/Me$_2$SiCl$_2$ ratio | 0.056 | 0.053 | 0.25 | 0.40 | 0.68 |

There has been described a copper catalyst having a high activity suitable for use in the Rochow reaction of directly reacting an organic halide with metallic silicon powder to synthesize organohalosilanes. The inventive catalyst is successful in sustaining the high activity in the steady state, which has been the neck of the Rochow reaction, thus minimizing the formation of silane by-products due to side reaction. Once deactivated, the inventive catalyst is quickly discharged out of the reaction system. Therefore, the inventive catalyst improves the silane selectivity in the steady state and permits the reaction time to be prolonged, thereby increasing the conversion rate of metallic silicon. All these are industrial advantages.

Japanese Patent Application No. 11-104693 is incorporated herein by reference.

Reasonable modifications and variations are possible from the foregoing disclosure without departing from either the spirit or scope of the present invention as defined by the claims.

What is claimed is:

1. A metallic copper catalyst for use in the synthesis of organohalosilanes, consisting of a metallic copper powder in flake form having a bulk specific gravity of 1 to 3 g/cm$^3$ and a mean particle size of 10 μm to 1 mm as measured by laser diffraction particle size distribution analysis.

2. The copper catalyst of claim 1 wherein the metallic copper powder is a copper foil powder or stamped copper powder having a specific surface area of 0.1 to 2 m$^2$/g as measured by the BET method or air permeability method.

3. A process for preparing organohalosilanes, comprising the step of reacting an organic halide with metallic silicon particles in the presence of the metallic copper catalyst of claim 1.

* * * * *